United States Patent [19]

Shaw et al.

[11] Patent Number: 5,134,130
[45] Date of Patent: Jul. 28, 1992

[54] LIPID EMULSION FOR TREATING AIDS

[75] Inventors: Howard L. Shaw, Deerfield, Ill.; Jeffrey Askanazi, Wayne, N.J.; William D. Leathem, Lindenhurst, Ill.

[73] Assignee: Abbott Laboratories, Abbott Park, Ill.

[21] Appl. No.: 751,597

[22] Filed: Aug. 21, 1991

Related U.S. Application Data

[63] Continuation of Ser. No. 276,181, Nov. 23, 1988, abandoned.

[51] Int. Cl.$^5$ .................... A61K 9/107; A61K 31/685
[52] U.S. Cl. ........................................ 514/78; 514/938
[58] Field of Search ................................. 514/77, 78

[56] References Cited

U.S. PATENT DOCUMENTS

| | | | |
|---|---|---|---|
| 3,169,094 | 2/1965 | Wretlind | 514/783 |
| 4,073,943 | 2/1978 | Wretlind | 514/283 |
| 4,101,673 | 2/1965 | Chang | 514/938 |
| 4,157,404 | 6/1979 | Yano et al. | 476/471 |
| 4,372,949 | 2/1983 | Kodama et al. | 424/199 |
| 4,465,693 | 8/1984 | Strauss et al. | 424/199 |
| 4,474,773 | 10/1984 | Shinitzky et al. | 424/199 |
| 4,677,099 | 6/1987 | Shinitzky et al. | 514/78 |
| 4,711,902 | 12/1987 | Serno | 514/937 |

FOREIGN PATENT DOCUMENTS

| | | |
|---|---|---|
| 211257 | 2/1987 | European Pat. Off. |
| 0213724 | 11/1987 | European Pat. Off. |
| WO8701592 | 3/1987 | PCT Int'l Appl. |

OTHER PUBLICATIONS

Groves, Chem. Abs. 103, 27187.
Change, II, Chem. Abs. 84, 169684 (1974).
"Body composition studies in patients with the acquired immunodeficiency syndrome[1-3]"; Donald P. Kotler, MD, Jack Wang, MS, and Richard N. Pierson, Jr., MD; the American Journal of Clinical Nutrition 42: Dec. 1985, pp. 1255-1265.
"Does Nutritional Deficiency Predispose to Acquired Immune Deficiency Syndrome?"; V. K. Jain, M. B. B. S. and R. K. Chandra, M.D., F.R.C.P.; Nutrition Research, vol. 4, pp. 537-543, 1984.
"High Density Lipoprotein As a Protective Factor Against Coronary Heart Disease"; T. Gordon, W. P. Castelli, M.D., M. C. Hjortland, Ph.D., W. B. Kannel, M.D., T. R. Dawber, M.D.; The American Journal of Medicine, vol. 62, May 1977.
"Enteropathy Associated with the Acquired Immunodeficiency Syndrome"; D. P. Kotler, M.D., H. P. Gaetz, M.D., M. Lange, M.D., E. B. Klein, M.D., and P. R. Holt, M.D.; Annals of Internal Medicine, Oct. 1984, vol. 101, No. 4.
"Response to Total Parenteral Nutrition in the Extremely Malnourished Patient"; P. M. Starker, M.D., P. A. LaSala, M.D., R. Armour Forse, M.D., Ph.D., J. Askanazi, M.D., D. H. Elwyn, Ph.D., and J. M. Kinney, M.D.; Journal of Parenteral and Enteral Nutrition, vol. 9, No. 3, Accepted for publication Nov. 10, 1984.
Correspondence "Effects of a novel Compound (AL 721) on HTLV-III Infectivity in Vitro"; P. S. Sarin, R. C. Gallo, D. I. Scheer, F. Crews, A. S. Lippa; The New England Journal of Medicine, Nov. 14, 1985, pp. 1289-1290.
"Lipid composition and fluidity of the human immunodeficiency virus"; Roland C. Aloia et al.; Medical Sciences, vol. 85, pp. 900-904, Feb. 1988.
"Interaction of Vesicular Stomatitis Virus with Lipid Vesicles: Depletion of Cholesterol and Effect on Virion Membrane Fluidity and Infectivity"; N. F. Moore et al.; Journal of Virology, Aug. 1978, pp. 320-329.
"A special lipid mixture for membrane fluidization"; M. Lyte and M. Shinitzky; 1985 Elsevier Science Publishers B.V., pp. 133-138.
"Human Immunodeficiency Virus (HIV-1) Cytotoxicity: Perturbation of the Cell Membrane and Depression of Phospholipid Synthesis"; William S. Lynn et al.; Virology 163, pp. 43-51 (1988).

*Primary Examiner*—Mark L. Berch
*Attorney, Agent, or Firm*—Dressler, Goldsmith, Shoré, Sutker & Milnamow, Ltd.

[57] ABSTRACT

A composition for the treatment of patients having Acquired Immune Deficiency Syndrome comprising approximately 2 to 7 percent by weight soybean oil and approximately 1 to 2 percent by weight egg phosphatide and a method for the parenteral administration of this composition is disclosed.

1 Claim, No Drawings

LIPID EMULSION FOR TREATING AIDS

This application is a continuation of application Ser. No. 07/276,181, filed Nov. 23, 1988 now abandoned.

FIELD OF THE INVENTION

The present invention relates to a composition and method for treating patients with Acquired Immune Deficiency Syndrome. More particularly, this invention relates to a composition for the parenteral administration of a non- or low carbohydrate source of calories for nutritional support and phosphatides to stimulate prostaglandin synthesis.

BACKGROUND OF THE INVENTION

The number of patients suffering from Acquired Immune Deficiency Syndrome (AIDS) has increased dramatically since the first cases were reported a few years ago. The disease has caused opportunistic infections and secondary cancers in more than 50,000 people in the United States and many more throughout the world. Patients suffering from AIDS are often nutritionally unbalanced and wasted. Weight loss and decrease in serum albumin, total iron binding capacity and retinal binding protein are often seen. Body composition analysis in AIDS patients demonstrates a depletion in total body potassium and body fat content with an increase in extracellular water. These symptoms are often seen in those suffering from chronic malnutrition.

A number of factors lead to malnutrition in AIDS patients. These include a decrease in food intake, vomiting, the side effects of therapeutic drugs and a high incidence of malabsorption syndrome with or without diarrhea.

When malabsorption syndrome and/or diarrhea do not permit effective oral feeding, parenteral nutrition is indicated. Conventional parenteral nutrition compositions and methods of therapy are unbalanced attempts at nutritional restitution. They contain too high a fat content which, if administered too rapidly, can exacerbate the formation of pro-inflammatory prostanoids and prevent the beneficial effects of low-fatty acid administration. This invention permits administration of the desired level of egg phospholipids and triglycerides over a longer period of time without exacerbating pro-inflammatory prostanoids or inducing fat overload.

It is also known that some of the manifestations of AIDS are ameliorated by non-steroidal anti-inflammatory agents. It is believed that these effects are related to a preferential suppression of certain prostaglandins by these agents. Prostaglandins are synthesized in the body from fatty acid precursors which are derived from lipids. The composition, rate of administration and concentration of neutral lipids, fatty acids and lecithins administered parenterally can determine the prostaglandin synthetic pathway and thereby the specific class of eicosanoid being preferentially synthesized.

Thus, there is a need for a low fat - high phosphatide parenteral formulation for the treatment of AIDS patients either as a component of total parenteral nutrition of as a parenteral supplement to patients receiving nutrition orally.

SUMMARY OF THE INVENTION

In accordance with the present invention, there is provided a composition and a method for the treatment of AIDS patients which comprises parenterally administering to such patients a composition comprising a soybean oil emulsion containing egg phosphatide. More particularly, the compositions contain approximately 2 to 7 percent by weight soybean oil and approximately 1 to 2 percent by weight egg phosphatide. The compositions of this invention contain a higher egg phosphatide/triglyceride ratio, in comparison to commercially available fat emulsions, in the range of about 1:1 to 1:3 which makes it possible to provide a sufficient level of egg phosphatide to promote mobilization of tissue cholesterol without inducing fat overload.

DESCRIPTION OF THE PREFERRED EMBODIMENTS

The presently preferred parenteral compositions of this invention contain approximately 2 percent by weight soybean oil and approximately 1.2 percent by weight egg phosphatide.

The most preferred parenteral composition of the present invention contains the following:

| Ingredient | Per mL |
| --- | --- |
| Soybean Oil, Wiwnterized | 20 mg |
| Egg Phosphatide | 12 mg |
| Glycerin, USP | 25 mg |
| Nitrogen, USP | q.s. |
| Sodium Hydroxide | q.s. |
| Water | q.s. |

The soybean oil utilized in the composition of the present invention may be obtained from any commercially available source and should have a fatty acid composition of from about 44 to about 62 weight percent linoleic acid, from about 19 to about 30 weight percent oleic acid, from about 7 to about 14 weight percent palmitic acid, from about 1 to about 6 weight percent stearic acid, and from about 4 to about 11 weight percent linolenic acid. The egg phosphatide utilized in the composition of the present invention may also be obtained from commercially available sources and should preferably have a nitrogen to phosphorous molar ratio of from about 0.97 to about 1.17.

The composition of the present invention may be prepared in accordance with known procedures in the art as illustrated by the following example.

EXAMPLE 1

Water for injection (approximately 1 L) is heated and protected by a nitrogen atmosphere. Egg phosphatide (12 g) is added to the water and dispersed by agitation at a temperature in the range of 50° to 90° C. Glycerin (25 g) is filtered through an 0.8 micrometer membrane filter and added to the dispersion using a Manton-Gaulin homogenizer to finely divide the egg phosphatide and increase the degree of dispersion. The aqueous phosphatide dispersion is then filtered through a nylon or equivalent membrane of 0.45 micrometer porosity and the pH is adjusted to a range of 8.5 to 10.5 with sodium hydroxide. Soybean oil, winterized, (20 g) is filtered through a 0.45 micrometer membrane, heated to a temperature in the range of 55° to 95° C. and added to the egg phosphatide dispersion with agitation to form a coarse emulsion concentrate which is then homogenized using a Manton-Gaulin homogenizer at a pressure of 2000 to 5000 psi. The pH is then adjusted to a range of 8.5 to 9.5, if necessary, with sodium hydroxide and the emulsion is filtered through a nylon membrane of at least 0.8 micrometer porosity with sufficient surface area to provide minimum restriction of flow. The emulsion is then further homogenized in a Manton-Gaulin homogenizer, diluted to a desired concentration with sterile water and the pH adjusted to A range of 8.5 to 9.6 with sodium hydroxide.

When used in treating patients with AIDS the emulsions of this invention should be administered parenterally in amounts sufficient to provide approximately 50 to 30 mL/Kg day.

What is claimed is:
1. A method for the treatment of malnutrition in a host mammal having Acquired Immune Deficiency Syndrome comprising parenterally administering to said mammal a therapeutically effective amount of a composition comprising about 2 percent by weight soybean oil, about 1.2 percent by weight egg phosphatide and about 2.5 percent by weight glycerol, said composition having a ratio of egg phosphatide to soybean oil of about 1:1.67.

* * * * *